(12) United States Patent
Härtel

(10) Patent No.: US 11,446,206 B2
(45) Date of Patent: Sep. 20, 2022

(54) CONTAINER FOR MEDICAL LIQUIDS AND METHOD FOR FILLING A CONTAINER OF THIS TYPE

(71) Applicant: VETTER PHARMA-FERTIGUNG GMBH & CO. KG, Ravensburg (DE)

(72) Inventor: Ulrich Härtel, Kisslegg (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 114 days.

(21) Appl. No.: 16/955,292

(22) PCT Filed: Dec. 19, 2018

(86) PCT No.: PCT/EP2018/086000
§ 371 (c)(1),
(2) Date: Jun. 18, 2020

(87) PCT Pub. No.: WO2019/122024
PCT Pub. Date: Jun. 27, 2019

(65) Prior Publication Data
US 2020/0390652 A1 Dec. 17, 2020

(30) Foreign Application Priority Data
Dec. 21, 2017 (DE) .................... 10 2017 223 505.5

(51) Int. Cl.
*A61J 1/06* (2006.01)
*A61J 1/14* (2006.01)
*B65B 3/00* (2006.01)

(52) U.S. Cl.
CPC .............. *A61J 1/062* (2013.01); *A61J 1/1412* (2013.01); *B65B 3/003* (2013.01)

(58) Field of Classification Search
CPC ........ A61J 1/062; A61J 1/1412; A61J 1/1443; A61J 1/1456; B65B 3/003
(Continued)

(56) References Cited

U.S. PATENT DOCUMENTS 3,970,219 A * 7/1976 Spitzer ................... B65D 83/62
                                                            222/1
5,993,425 A * 11/1999 Kriesel ................. A61M 5/152
                                                          604/132
(Continued)

FOREIGN PATENT DOCUMENTS

| CA | 2362260 C | 5/2009 |
|----|-----------|--------|
| DE | 102009051945 A1 | 5/2011 |
| WO | 2011014514 A1 | 2/2011 |

OTHER PUBLICATIONS

International Preliminary Report on Patentability received for the PCT Application No. PCT/EP2018/086000, dated Jul. 2, 2020, 8 pages.
(Continued)

*Primary Examiner* — Timothy L Maust
(74) *Attorney, Agent, or Firm* — Harness, Dickey & Pierce, P.L.C.; Stephen T. Olson

(57) ABSTRACT

A container for medical liquids comprises an inner container having a distal end and a proximal end, a first porous separating element being arranged at the proximal end, the first porous separating element delimiting a holding volume for holding a medical liquid, and comprising an outer container, in which the inner container is arranged with the proximal end and with at least portions of the holding volume. The outer container extends around the inner container gas-tight such that a gas under positive pressure can be arranged in a peripheral volume arranged between an outer surface of the inner container and an inner surface of the outer container. An outlet channel section is connected to the distal end of the inner container. At least portions of the outlet channel section are arranged outside of the outer container. A valve device can be arranged in the outlet channel section, which valve device is designed, in an open position, to open a fluid connection between a distal outlet
(Continued)

opening of the outlet channel section and the holding volume and, in a closed position, to block the fluid connection between the distal outlet opening and the holding volume.

20 Claims, 2 Drawing Sheets

(58) Field of Classification Search
 USPC .......................................................... 141/20
 See application file for complete search history.

(56) References Cited

U.S. PATENT DOCUMENTS

| | | |
|---|---|---|
| 9,744,296 B2 | 8/2017 | Fini et al. |
| 2012/0226236 A1 | 9/2012 | Fini et al. |

OTHER PUBLICATIONS

International Search Report (in English and German) and Written Opinion of the ISA (in German) issued in PCT/EP2018/086000, dated Apr. 4, 2019; ISA/EP.

* cited by examiner

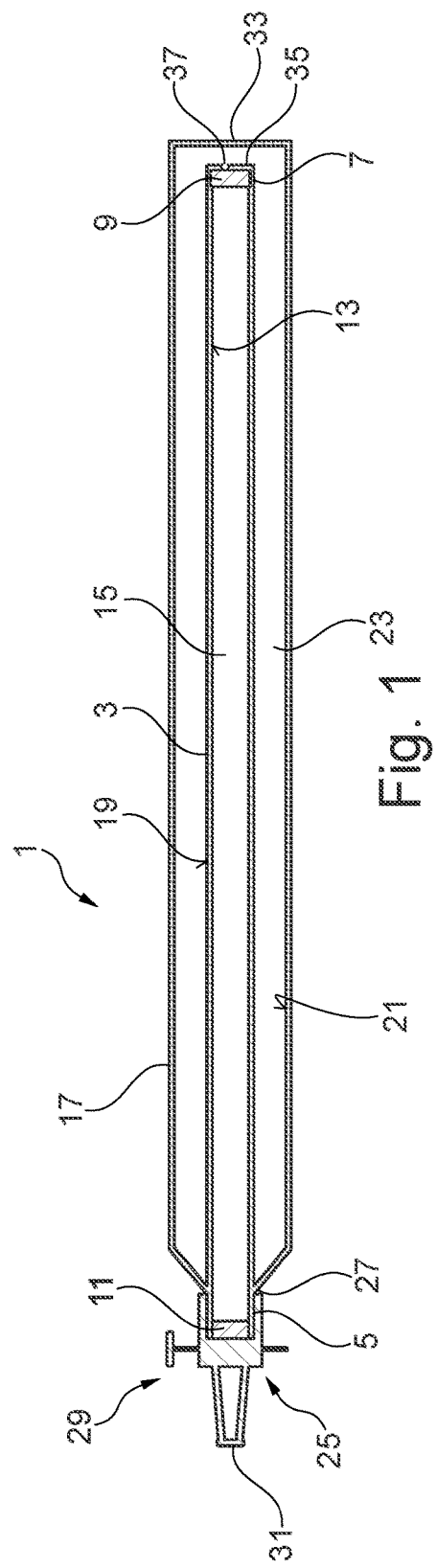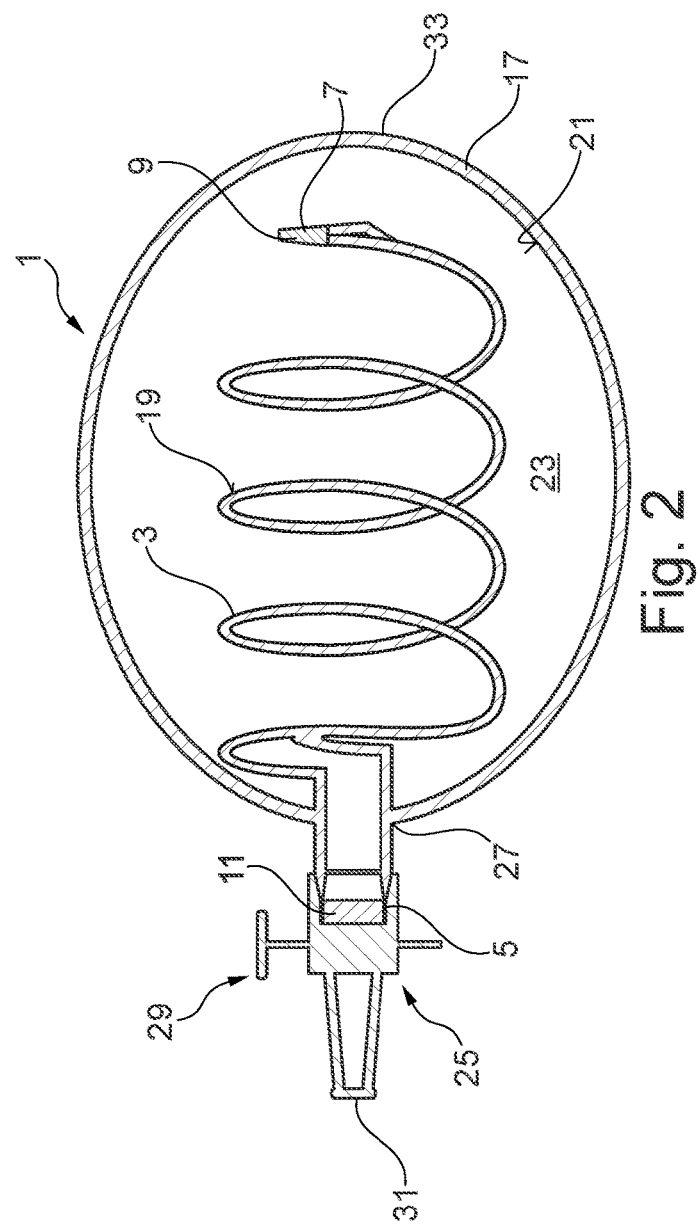

CONTAINER FOR MEDICAL LIQUIDS AND METHOD FOR FILLING A CONTAINER OF THIS TYPE

CROSS-REFERENCE TO RELATED APPLICATIONS

This application is a 371 U.S. National Phase of International Application No. PCT/EP2018/086000, filed Dec. 19, 2018, which claims the benefit of German Patent Application No. 10 2017 223 505.5, filed Dec. 21, 2017. The entire disclosures of the above applications are incorporated herein by reference.

The invention relates to a container for medical liquids and to a method for filling a container of this type.

Containers for medical liquids are known in particular in the form of prefilled syringes or cartridges. These have at least one displaceable stopper, usually made of a pharmaceutical rubber, which can be moved in such a medical container by hand power, by a motor drive or also pressure-operated in order to expel from the container a medical liquid arranged in the container. In particular in the case of hand-powered medical containers, there are shortcomings in ergonomics and handling. With a conventional syringe, especially when a patient must give himself an injection, this is only possible in a cumbersome manner and with an unergonomic hand position. The highly precise provision and metering of small volumes, in particular less than 0.5 mL, in conventional prefilled syringes or cartridges is also problematic. In the case of such small quantities in particular, it is hardly possible to precisely measure the volume ultimately injected. Multiple applications are problematic with conventional containers, particularly because of the formation of air bubbles and the resulting risk of air embolism. Pharmaceutical rubbers used to form conventional stoppers are permeable to oxygen, making them poorly suited for storing medical liquids sensitive to oxygen, such as adrenaline. In addition, such stoppers require a lubricant, in particular silicone oil, for low-friction displacement, in particular in a glass container, which can result in an undesirable exposure of the patient to the lubricant. Furthermore, such conventional containers have problems with regard to the tightness of their seals under vacuum and/or pressure loads. Since the forces introduced into the stopper to dispense the medical liquid naturally fluctuate, particularly in manual operation, defined flow rates of the medical liquid can hardly be guaranteed when dispensing from the container. If there is a need to remove an air bubble from the container before the injection, there is almost inevitably also an undesirable leakage of medical liquid when the air bubble is expelled. Last but not least, this contributes to the fact that, in particular, small volumes can hardly be metered precisely with conventional containers.

The invention has for its object to provide a container for medical liquids and a method for filling a container of this type, wherein the disadvantages mentioned do not occur.

The object is achieved by creating the subject matters of the independent claims. Advantageous embodiments are described in the dependent claims.

The object is achieved in particular by creating a container for medical liquids, comprising an inner container which itself has a distal end and a proximal end. A first, proximal porous separating element is arranged at the proximal end. The first porous separating element delimits a holding volume for holding a medical liquid. The container also comprises an outer container in which the inner container is arranged with the proximal end and with at least portions of the holding volume, wherein the outer container extends around the inner container in a gas-tight manner, such that a gas under excess positive pressure can be arranged in a peripheral volume of the outer container between an outer surface of the inner container and an inner surface of the outer container, and in particular the holding volume has a pressure-transmitting connection with the peripheral volume via the first porous separating element. An outlet channel section of the container is connected to the distal end of the inner container, wherein at least portions of the outlet channel section are arranged outside the outer container. A valve device can be arranged, and preferably is arranged, in the outlet channel section, and is configured, in an open position, to open a fluid connection between a distal outlet opening of the outlet channel section and the holding volume, and, in a closed position, to block the fluid connection between the distal outlet opening and the holding volume. A medical liquid can be held and stored in the holding volume and can be expelled through the distal outlet opening via the outlet channel section and the valve device by means of the gas arranged under positive pressure in the peripheral volume, which acts on the medical liquid via the first, proximal porous separating element when the valve device is moved from its closed position to its open position. This does not require a movable stopper to be moved in the container—specifically, neither in the inner container nor in the outer container. Rather, the medicinal liquid is expelled exclusively by the gas under positive pressure in the peripheral volume. Actuators, or a manual displacement of a displaceable stopper, can thus be completely dispensed with, so that the container can be used ergonomically, reproducibly and in a simple manner for an injection. Due to the positive pressure in the peripheral volume, there is also a defined flow rate for the medical liquid emerging from the container. This liquid can be dispensed with high accuracy via the valve device, so that even small volumes can be dosed with high precision. The defined flow rate can be constant over time over the course of the injection, or can vary in a certain way. A multiple-use application is easily possible with the aid of the valve device when the latter, after the dosing of a first desired volume of the medical liquid which is smaller than the holding volume, is moved from the open position back to the closed position, after which it can be moved again from the closed position to the open position for a further injection. This can be repeated several times and as often as desired until the medical liquid has been completely dispensed from the holding volume. Depending on the gas arranged in the peripheral volume, the container can also easily be used for oxygen-sensitive medical liquids, for example adrenaline, in particular if a low-oxygen or even oxygen-free gas is arranged in the peripheral volume.

A distal direction is understood to mean in particular a direction which points in the direction of outflow of the medical liquid from the container, in particular when the container is oriented as intended in the direction of an injection target, that is to say in particular a body of a patient, for example. A proximal direction is understood to mean an opposing direction, which points counter to the intended outflow direction of the medical liquid from the container.

A second porous separating element is preferably arranged at the distal end of the inner container, the first porous separating element and the second porous separating element delimiting the holding volume. The medical liquid can then be held, and preferably is held, in particular in the holding volume between the first porous separating element and the second porous separating element. It can be expelled through the distal outlet opening via the second, distal porous separating element, the outlet channel section and the valve device.

The first porous separating element preferably closes off the inner container at its proximal end, in particular directly at its proximal end. The second, distal separating element preferably also closes off the inner container at its distal end, in particular directly at its distal end, in particular if the outlet channel section is formed in several parts with the inner container. However, it is also possible for the outlet channel section to be arranged as a single piece with the inner container. In this case, the inner container continues, so to speak, in the outlet channel section, such that in this case the distal end of the inner container is to be regarded as an imaginary distal end, which essentially represents the distal end of the holding volume. This imaginary distal end, and thus at the same time a distal boundary of the holding volume, are spaced apart from the distal outlet opening of the outlet channel section as viewed in the proximal direction.

The at least one porous separating element, namely the first porous separating element and preferably the second porous separating element, is/are preferably arranged fixed in place relative to the inner container. In particular, the separating elements are preferably not displaceable relative to the inner container. Rather, the separating elements are preferably fixed in place on the inner container. The separating elements are therefore in particular not displaceable stoppers.

Alternatively, however, it is also possible for at least one of the porous separating elements to be displaceable. In particular, the proximal porous separating element can be arranged displaceably in the inner container and can preferably move, during the expulsion of the medical liquid, with its proximal boundary surface. This can contribute in a particularly advantageous manner to preventing the formation of an air bubble. The second, distal separating element can alternatively or additionally be releasably attachable to the inner container, in particular together with the outlet channel section. In particular, the second separating element can be part of the outlet channel section or can be firmly connected to it. The second separating element can also be integrated in a tamper-evident closure or in a push-on cannula.

The container is preferably free of a displaceable stopper; it therefore preferably has no displaceable stopper, in particular no displaceable stopper made of a pharmaceutical rubber. In principle, however, it is also possible to additionally provide a displaceable stopper, in particular between the first separating element and the second separating element in the inner container.

The first porous separating element and the second porous separating element delimit the holding volume, in particular together with a wall, in particular an inner wall, of the inner container, the wall in particular forming an inner shell surface which encompasses the holding volume, wherein the porous separating elements in each case form end boundaries of the holding volume.

The peripheral volume is preferably at least as large as the holding volume. The gas volume in the peripheral volume thus corresponds in particular to at least the volume of the medical liquid in the inner container between the porous separating elements, so that a continuous, undisturbed outflow of the medical liquid—preferably with a defined flow rate—from the container is ensured over the entire expulsion of the complete contents of the holding volume.

The fact that the gas is arranged under positive pressure in the peripheral volume means in particular that the gas is arranged under a pressure in the peripheral volume which is greater than an ambient pressure of the container, in particular as a normal pressure, preferably greater than 1013 mbar. The positive pressure is preferably set such that a desired expulsion behavior for the medical liquid from the holding volume is achieved. This applies in particular to a predetermined flow rate for the medical liquid.

The outlet channel section is connected to the distal end of the inner container, in particular in a manner allowing flow, wherein it is preferably separated from the peripheral volume, in a manner prohibiting flow. This means in particular that there is no direct fluid connection between the outlet channel section on the one hand and the peripheral volume on the other. Such a fluid connection is at most mediated via preferably the distal separating element, the holding volume and the proximal separating element, gas from the peripheral volume being able to penetrate into the holding volume in order to expel the medical liquid, which in turn can emerge preferably via the distal separating element into the outlet channel section, and finally via the distal outlet opening.

In a preferred embodiment it is provided that the inner container and/or the outer container comprise(s) glass, or consist(s) of glass. In this way, in particular, permanently pressure-stable containers can be provided which are, in any case, gas-impermeable to an external environment of the container. However, the inner container and/or the outer container can also comprise a metal or a metal alloy, plastic or ceramic, or consist of a metal or a metal alloy, plastic or ceramic.

The valve device is preferably designed as a tamper-evident closure, so that opening the valve device for the first time leads to an irreversible change in it, which can be easily recognized later. For example, breakable webs, membranes or the like can be provided on the valve device, which break or tear when actuated for the first time.

A cannula, a syringe needle or the like can preferably be fixedly arranged on the distal outlet opening of the outlet channel section. However, it is also possible for the distal outlet opening to be arranged on a connection element of the outlet channel section for an injection device, for example for a fixed cannula, a syringe needle, an infusion set, for example an infusion tube, or the like. In particular, the distal outlet opening can be formed on a Luer lock connection which the outlet channel section comprises.

Alternatively or additionally, it is preferably provided that the inner container is elongated. The extension of the inner container thus defines in particular a longitudinal direction which points from the distal end to the proximal end.

Alternatively or additionally, it is preferably provided that the inner container is straight, in particular cylindrical. This represents a particularly simple and particularly inexpensive form of the inner container. The inner container is particularly preferably of circular cylindrical design.

As an alternative or in addition, it is preferably provided that the inner container is drawn, and in particular is spiral. The inner container is particularly preferably wound around an axis which points in the direction of its longest extension. In this way, the overall length of the container can be shortened compared to a container having a straight inner container of equal length measured along its profile.

According to a development of the invention, it is provided that the inner container is designed as a capillary. This means, in particular, that the inner shell surface which delimits the holding volume is dimensioned as a function of an interaction of the medical liquid with the material of the inner container, in particular the inner shell surface, and as a function of the surface tension of the medical liquid, such that the medical liquid is conveyed into the holding volume by capillary forces when the container is filled, and at the same time the liquid is completely filled to the proximal porous separating element. In the case of a cylindrical inner container with a given length, the inner shell surface is determined in particular by the inner diameter or inner radius of the inner container, which is then dimensioned accordingly. The design of the inner container as a capillary also requires a comparatively small inner diameter, such that even a small holding volume can extend over a clearly perceptible length of the inner container, and a scale can be arranged in a simple manner here so that doses of smaller volumes can also be determined easily with the naked eye. An injection is therefore easy to execute. In particular, the length of the inner container is preferably several times greater than the inner diameter.

If the capillary forces of the inner container are negligible, an injection with a vertical orientation of the container can also be possible.

The inner container particularly preferably has an inner diameter of less than 10 mm, preferably of less than 8 mm, preferably of at most 4 mm, preferably of less than 4 mm, preferably of at most 3 mm, preferably of less than 3 mm, particularly preferably of at least 2 mm to a maximum of 3 mm.

According to a development of the invention, it is provided that the outlet channel section is formed integrally with the inner container. The outlet channel section with the inner container is particularly preferably designed as a one-piece glass part, the second, distal porous separating element preferably representing a separation between the inner container and the outlet channel section, wherein the latter is preferably arranged in the interior of the one-piece arrangement of the outlet channel section and the inner container, offset from the distal outlet opening in the proximal direction.

Alternatively, it is preferably provided that the outlet channel section is formed in several parts with the inner container. In particular, the outlet channel section can be designed as an attachment to the inner container, and can be plugged on to the same in a liquid-tight manner, in particular onto the distal end of the inner container, or can be connected in a liquid-tight manner in another way to the distal end of the inner container. The outlet channel section is particularly preferably designed as a plastic attachment. This can thus be produced particularly inexpensively, for example by means of an injection molding process.

Regardless of whether the outlet channel section is formed in one piece or in several pieces with the inner container, the outlet channel section preferably has a receptacle for the valve device, which can be designed in particular as a bore penetrating the outlet channel section in the transverse direction—transverse to the outflow direction of the medical liquid from the distal outlet opening.

According to a development of the invention, it is provided that the first porous separating element and/or the second porous separating element is/are designed as a sintered body. Such a porous separating element is preferably formed from a plurality of particles which are integrally bonded to each other in only some regions thereof. Such a sintered body is preferably produced by heating the particles, the same contacting each other, in some regions to a softening temperature, preferably below a melting temperature, so that they soften in the edge regions or become partially molten, so that they bond to one another, particularly in the region of their contact points. In particular, the nearest neighbors of the particles partially bond to each other. Fine channels, which in particular function like capillaries, remain between the particles. A particularly preferred embodiment of such a sintered body is a frit, wherein the first porous separating element and/or the second porous separating element is/are in particular designed as a frit, preferably as a glass frit or ceramic frit.

However, it is also possible for the first porous separating element and/or the second porous separating element to be designed as a filter or filter membrane, in particular having a pore diameter of at least 0.5 μm to at most 3 μm, preferably from at least 1 μm to at most 2 μm, preferably 1.6 μm. At least one of the separating elements preferably has a bubble point of at least 0.1 bar to at most 0.7 bar, preferably of 0.4 bar.

Such sintered bodies have filter properties, so that particles present in the medical liquid can be filtered, in particular by the distal porous separating element, either when the container is being filled with the medical liquid or when the medical liquid is subsequently expelled from the container. This is particularly favorable in the context of medical liquids for ophthalmic use, since no or only a small number of very small particles may be introduced into the vitreous body of the eye.

The porous separating elements also fulfill the following important functions: During filling of the medical container, capillary forces in the area of the first, proximal, porous separating element prevent the medical liquid from escaping from the holding volume into the peripheral volume; the capillary forces prevailing, on the one hand, in the inner container, and on the other hand in the region of the first porous separating element, result in a complete, airless filling of the holding volume. Furthermore, the first porous separating element has the task of transmitting the positive pressure of the gas in the peripheral volume to the liquid, so that the latter can be expelled via the distal outlet opening when the valve device is opened. The distal porous separating element very efficiently prevents the injection of air bubbles, since the medical liquid stops escaping through the distal porous separating element as soon as it no longer comes into contact with liquid arranged in the holding volume, and comes into contact with an air bubble or gas present there. Undesired injection of gas can therefore be effectively prevented.

The first separating element and the second separating element preferably have different pore sizes or pore diameters from one another in order to ensure that, on the one hand, gas can pass through the first, proximal separating element in order to effect the injection, and on the other hand an injection of gas through the second, distal separating element is prevented. In particular, the first separating element and the second separating element have different bubble points and thus different passage properties for gases.

However, since the pressure in the peripheral volume decreases in the course of the injection, it is also possible for the separating elements to have the same pore diameter and/or bubble points, wherein the first separating element allows gas to pass through at the higher gas pressure at the start of the injection, but the second separating element prevents gas passage at the end of the injection at the then-lower gas pressure.

If the porous separating elements are designed as glass frits, they are preferably fused into the inner container by melting. This is possible in a particularly stable and inexpensive manner if the inner container also comprises glass or consists of glass.

Forming the inner container from glass has the additional advantage that it is highly chemically inert to the medical liquid. Since no displaceable stopper is provided in the inner container, no use of a lubricant, in particular no silicone oil, is required. The medical liquid can thus be stored in the inner container at high purity without any risk of contamination.

According to a development of the invention, it is provided that the distal porous separating element is arranged outside the outer container. A connection point at which the outer container is connected in a gas-tight manner to the inner container, preferably fused, is accordingly offset in the proximal direction with respect to the distal porous separating element. However, it is also possible for the distal porous separating element to be arranged inside the outer container or precisely in the region of the connection point between the outer container and the inner container.

According to a development of the invention, it is provided that the outer container is cylindrical. This represents a simple and in particular easy-to-manufacture design of the outer container.

Alternatively or additionally, it is preferably provided that the outer container is barrel-shaped or piston-shaped. This means in particular that the outer container can have a wall curved in two mutually perpendicular directions. Such a configuration helps to avoid sharp-angled transitions, so that the outer container can be designed to be particularly pressure-stable.

Alternatively or additionally, the outer container is preferably convex, wherein this indication of a convex design is relative to the direction of view of an observer of the outer container from the outside. The outer wall of the outer container thus has, in particular globally, an outward curvature or bulge. This also contributes to a particularly pressure-stable outer container.

Alternatively or additionally, it is preferably provided that the outer container is ovoid or oval. This results in a particularly favorable, very pressure-stable shape of the outer container, which can be designed, in particular, as an essentially egg-shaped or light bulb-shaped body.

According to a development of the invention, it is provided that the outlet channel section is arranged at a finite angle other than 0° to a primary direction of extension of the inner container. In particular, a longitudinal direction of the outlet channel section, that is to say in particular an outlet direction or longitudinal direction of an outlet section which has the distal outlet opening, of the outlet channel section extends at a finite angle other than 0° to the primary direction of extension of the inner container. The primary direction of extension of the inner container is, in particular, a cylinder axis or longitudinal axis of the inner container, if the latter is cylindrical, or a direction of the longest dimension of the inner container around which the inner container can, for example, be drawn, in particular spirally, at least in some areas.

Since the outlet channel section forms an angle other than 0° with the primary direction of extension of the inner container, the container can essentially have the shape of a pistol, such that, on the one hand, the container can be held easily and ergonomically with one hand of a user, and on the other hand the valve device can be operated easily and ergonomically with a natural hand position, in particular with a finger of the hand holding the container. In this way, it is easy for a patient to give himself an injection with the container without much effort.

According to a development of the invention, it is provided that the container has a finger trigger that is operatively connected to the valve device in such a way that the valve device can be actuated by means of the finger trigger. In this way, the valve device can be actuated particularly ergonomically by a user with his finger. It is particularly preferred that the outlet channel section is arranged at a finite angle, other than 0° with respect to the primary direction of extension of the inner container, wherein the container also comprises the finger trigger with which the valve device can be actuated. The finger trigger acts like a pistol trigger which can be operated easily and ergonomically. This has great advantages, in particular with regard to a simple, straightforward self-injection of a patient. The finger trigger can in particular have a simple, curved bend element like a pistol. However, it is also possible for the finger trigger to have a finger ring, in particular a closed finger ring, through which the user of the container can extend his finger. In addition to opening the valve device, the finger ring also enables closing by moving the finger trigger back in a particularly simple manner, with no need to reach around it.

According to a further development of the invention, it is provided that the valve device has a check valve, a manually operated valve, a switching valve, and/or a combination valve comprising a check valve and a manually operated valve. A check valve proves to be particularly advantageous when filling the container; the medical liquid can be introduced into the holding volume under a pressure which slightly exceeds the positive pressure of the gas, with the check valve opening in this functional state. In the normal storage state, the gas in the peripheral volume and the medical liquid in the holding volume are then kept under this positive pressure, which forces the check valve into its sealing seat against the normal pressure acting in an external environment of the container.

A manually operated valve can be easily opened and closed by a user, so that dispensing of the medical liquid via the distal outlet opening can be easily controlled. However, a switching valve can also be used for this purpose, in particular if the valve device has an electronic control device designed to control such a switching valve.

A combination valve comprising a non-return valve and a manually operated valve is particularly preferred, the combination valve fulfilling the function of simply filling and securely holding the medical liquid in the container by means of the component of the non-return valve, while at the same time performing the function of easily opening and closing the valve device by means of the manually operated valve component. The manually operated valve component and the check valve are preferably formed integrally with one another. The manually operated valve particularly preferably has a seat for the check valve, this seat simultaneously providing a flow channel for the fluid connection between the holding volume and the distal outlet opening. In particular, the manually operated valve can have a recess which, in the closed position, has a seat for a valve element of the check valve, this recess being pivoted in the open position in such a way that it acts as a channel for the fluid connection between the holding volume and the distal outlet opening.

In particular, it is possible for the manually operated valve to have a pivotable cylinder arranged obliquely to, preferably perpendicularly to the outlet direction of the medical liquid from the container, and which has a recess which, in the closed position, is pivoted in the direction of the holding volume and is designed to form a sealing seat for the valve element of the check valve. In the open position, this recess is pivoted, preferably by 90°, in such a way that a liquid path between the holding volume and the distal outlet opening is opened via this recess. The valve element of the check valve is at the same time pushed against the sealing direction in the direction of the holding volume by the otherwise not-recessed outer circumferential surface of the cylinder of the manually operated valve, so that here too the fluid connection between the holding volume and the distal outlet opening is established. If the cylinder is pivoted back into the closed position, the valve element of the check valve can in turn be received tightly in the recess, so that the fluid connection between the holding volume and the distal outlet opening is blocked again.

The valve device preferably comprises a plastic or is formed from a plastic. This can be polyether ether ketone (PEEK), this material being inert on the one hand and very lubricious on the other hand—wherein it also provides a good sealing effect. There may then be no need for additional lubricants and/or sealing agents for the valve device. It is also possible that, for example, the cylinder of the manually operated valve is sealed with O-rings, and is preferably held and guided. Additionally or alternatively, it is possible that at least one wax-like sealant is used in the region of the valve device in order to seal the container from an exterior, in particular in the closed position of the valve, and/or to seal the fluid connection between the holding volume and the distal outlet opening with respect to the exterior of the container, such that the medical liquid can only escape laterally through the distal outlet opening and not through any gaps in the region of the valve device.

It is possible that the valve element of the check valve is biased into its closed position, for example with a spring element or another suitable biasing element. However, it is also possible that the valve device does not have such a biasing element, in which case the pressure difference between the pressure in the holding volume and the peripheral volume, on the one hand, and the pressure in the external environment of the container on the other hand are sufficient to force the valve element of the check valve into its seat.

According to a preferred embodiment, the further or differently configured valve device is also biased in its closing direction. For example, it is possible that the manually operated valve regardless of whether it is designed as a combination valve in its own right or in combination with the check valve—is biased into its closed position, for example by means of a biasing element, in particular a spring, which engages with an actuating lever or the finger trigger described above. The valve device is then opened against the biasing force, the valve device preferably being closed automatically as soon as a user releases or opens the valve device.

According to a development of the invention, it is provided that the inner container is filled with a medical liquid, the outer container being filled with a gas under positive pressure. The advantages described so far are realized in such a case. In particular, it is possible for the inner container to be filled with an oxygen-sensitive medical liquid, which can then be safely stored in the container over the long term if an oxygen-poor or oxygen-free gas is used as the gas in the outer container. In principle, any gas which does not react with the medical liquid, for example air, nitrogen, an inert gas, in particular an inert noble gas, can be used as the gas in the outer container.

According to a development of the invention, it is provided that the first, proximal porous separating element is covered at least in regions with respect to the peripheral volume of the outer container by a cover element, the cover element preferably covering the proximal porous separating element except for a central recess. The cover element advantageously allows a reduction in the contact area between the pressurized gas and the medical liquid, as a result of which, in particular, evaporation losses from the holding volume through the first, proximal porous separating element into the peripheral volume can be minimized. At the same time, the cover element offers protection against mechanical stress on the proximal porous separating element, and in particular protection against splashing if the container is exposed to a shock, for example if it is accidentally dropped.

The cover element is preferably designed as a cover cap, in particular having a central bore. Alternatively, it is also possible for the cover element to be designed as a membrane, preferably having a central recess.

As an alternative or in addition to a cover element, it is also possible for the first porous separating element to have an outer diameter which is smaller than the free inner diameter of the holding volume outside the proximal end of the inner container. In particular, the inner shell surface of the inner container can be thickened inward in the region of the proximal end, thus projecting radially inward, the first porous separating element being arranged in the region of the radial thickening. In this way too, the contact area between the gas and the medical liquid can be reduced, in particular minimized.

According to a development of the invention, it is provided that a predetermined breaking point is arranged at the distal connection point at which the outer container is connected in gas-tight manner to the inner container—in particular, fused to it. The predetermined breaking point is preferably designed such that when the container is exposed to an impact, in particular an impact due to falling, it enables the gas to escape in a controlled manner without a bang and without the medical liquid escaping. The predetermined breaking point can preferably be designed as a hole or bore, in particular transverse to a longitudinal axis of the container. If gas escapes transversely to the longitudinal axis, this leads at most to a rotation of the container, but not to a translational acceleration thereof, which in particular prevents the container from being accelerated like a rocket.

According to a development of the invention, it is provided that the container is designed as a syringe or carpule. The advantages of the container already described are realized in a special way in this case.

The holding volume preferably has a volume of less than 2 mL, preferably less than 1.5 mL, preferably less than 1 mL, preferably less than 0.6 mL, preferably less than 0.5 mL, wherein it is expediently configured to provide even small volumes for precise injection. The holding volume preferably has a hollow dimension of 1 mL. The container is particularly preferably configured for an ophthalmic injection, in particular into the vitreous body of an eye.

The container is also preferably set up to carry out a multiple-use injection, the valve device being able to be opened and closed as required, and the multiple-use injection being, for example, in different places, in particular in the case of subcutaneous or intramuscular application, and/or over a longer period, for example over a period of a month.

The container is particularly preferably designed to carry out a subcutaneous or intramuscular injection.

The object is also achieved by creating a method for filling a container for a medical liquid according to any one of the exemplary embodiments described above, the method comprising the following steps: The peripheral volume of the container is filled with a gas at a first predetermined pressure. The holding volume of the inner container is then filled with a medical liquid at a second predetermined pressure, the second predetermined pressure being greater than the first predetermined pressure, and finally the valve device is closed. In this way, the holding volume of the inner container in particular can be filled safely, reproducibly and completely.

It is particularly advantageous if the inner container is designed as a capillary, the capillary forces building up the column of medical liquid in the holding volume during filling, and at the same time holding it together later during emptying so that gas injection is effectively avoided.

The peripheral volume is preferably filled via the outlet channel section and the valve device as well as the inner container and the first, proximal porous separating element. In particular, the peripheral volume of the outer container is only accessible for filling in this way, while the outer container is otherwise completely gas-tight. The holding volume is also filled via the outlet channel section and the valve device. There is preferably no other access route to the holding volume.

If a gas other than air is used as the gas, the peripheral volume of the container is preferably evacuated several times—in particular via the outlet channel section and the valve device—and filled with pure gas to be used, so that the peripheral volume is sufficiently flushed. In this way, in particular, a low-oxygen or oxygen-free atmosphere can be provided in the peripheral volume.

The first predetermined pressure preferably corresponds to a predetermined final pressure for the later expulsion of the medical liquid from the container. As a result, the second predetermined pressure prevails as the initial pressure in the container after the valve device has been closed.

For filling, the container is preferably immersed, at least with the outlet channel section and in particular with the distal outlet opening, in the medical liquid or connected to a pressure connection to be supplied with the medical liquid. The filling then takes place automatically due to the second predetermined pressure, which is greater than the first predetermined pressure, and preferably due to the capillary forces acting in the inner container. These also ensure a complete and bubble-free filling of the holding volume, the filling automatically stopping as soon as the capillary forces prevent the medical liquid from escaping beyond the proximal, porous separating element into the peripheral volume.

If the external, second predetermined pressure is removed, the check valve of the valve device preferably closes automatically. A further valve component of the valve device, preferably a manually operated valve, can now either be installed additionally or—if it was already installed before filling—can be closed after filling.

During filling or before filling of the peripheral volume with the gas, a partial pressure, preferably in the gas, of at least one main constituent of the medical liquid, in particular of a solvent thereof, is preferably adjusted in such a manner that the partial pressure precisely corresponds to the vapor pressure of at least this main constituent of the medical liquid, or to the medical liquid in the inner container at the second predetermined pressure and thus the permanent storage pressure of the container 1. In this way, in particular the saturation vapor pressure of the medical liquid is set in the peripheral volume under storage conditions. This advantageously helps to prevent evaporation of at least components of the medical liquid via the proximal porous separating element into the peripheral volume, which in particular prevents the proximal porous separating element from drying out.

BRIEF DESCRIPTION OF THE DRAWINGS

The invention will be explained in more detail below with reference to the drawing, wherein:

FIG. 1 shows a schematic representation of a first embodiment of a container for medical liquids;

FIG. 2 show a schematic representation of a second embodiment of such a container;

DETAILED DESCRIPTION

Figure 3:
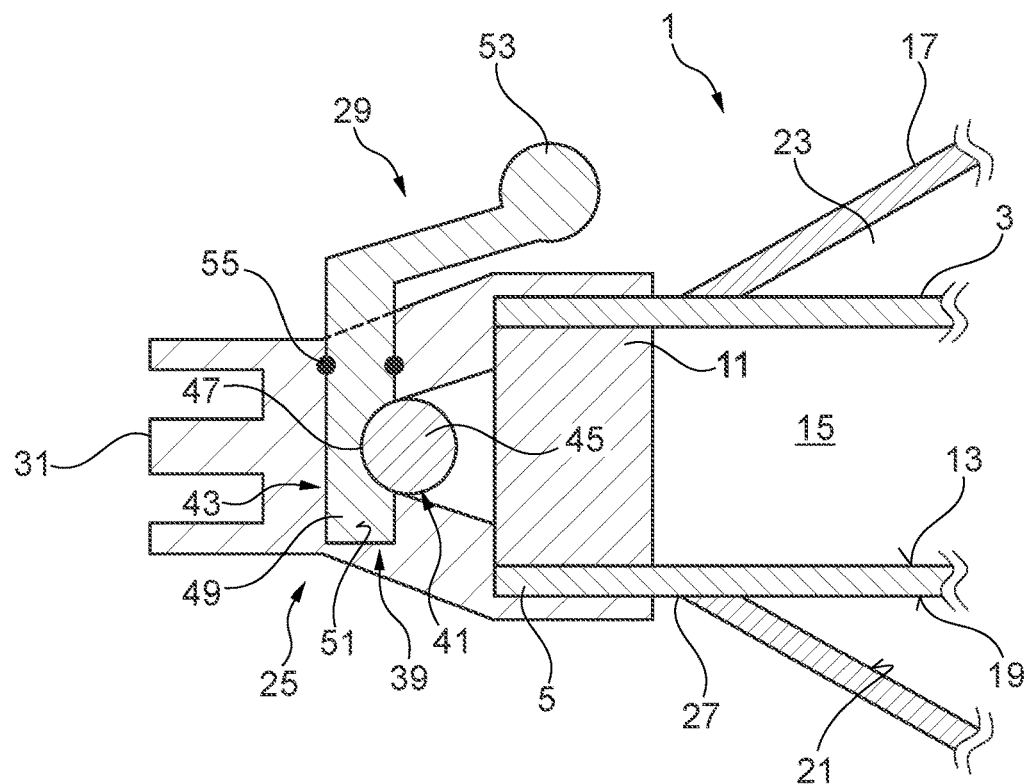
FIG. 3 shows a detailed view of an outlet channel section of a third embodiment of such a container.

FIG. 1 shows a schematic representation of a first embodiment of a container 1 for medical liquids, which is designed in particular as a syringe or cartridge. The container 1 has an inner container 3 with a distal end 5 and a proximal end 7. A first porous separating element 9 is arranged at the proximal end 7, and a second porous separating element 11 is preferably arranged at the distal end 5. The first porous separating element 9 and the second porous separating element 11 delimit—together with an inner shell surface 13 of the inner container 3—a holding volume 15 which is set up to receive a medical liquid, in particular a liquid medical active ingredient and/or excipient.

The container 1 also has an outer container 17, the inner container 3 being arranged in the outer container 17 with its proximal end 9 and at least partially with the holding volume 15. The outer container 17 surrounds the inner container 3 in a gas-tight manner, so that in a peripheral volume 23 arranged between an outer surface 19 of the inner container 3, which is in particular an outer shell surface, and an inner surface 21 of the outer container 17, a gas under positive pressure—relative to an external environment of the container 1—can be arranged.

The peripheral volume 23 is connected to the holding volume 15 via the first porous separating element 9, so that in particular the pressure prevailing in the peripheral volume 23 is transmitted to the holding volume 15.

An outlet channel section 25 is connected to the distal end 5 of the inner container 3 and is arranged at least partially outside the outer container 17, in particular distally to a connection point 27 at which the outer container 17 is connected in a gas-tight manner to the inner container 3, preferably fused to it.

A valve device 29 is arranged in the outlet channel section 25, and is configured to establish, in an open position, a fluid connection between a distal outlet opening 31 of the outlet channel section 25 and the holding volume 15, and, in a closed position, to block the fluid connection between the distal outlet opening 31 and the holding volume 15.

Both the inner container 3 and the outer container 17 are preferably formed from glass, in particular the inner container 3 from a—possibly drawn—glass tube or glass cylinder, which is straight in the embodiment of FIG. 1, and the outer container 17 from a glass tube or glass cylinder or a glass bulb, wherein the inner volume of the outer container 17 is adapted, relative to the inner container 3, so that the outer container 17 can at least accommodate portions of the inner container 3.

However, it is also possible that the inner container 3 and/or the outer container 17 comprise a plastic or are made of plastic. A ceramic or a metal or a metal alloy can also be used as the material for the inner container 3 and/or the outer container 17.

The inner container 3 preferably projects freely into the outer container 17 with its proximal end 7 and is in particular not connected to the outer container 17 at the proximal end 7. However, it is possible for a mechanical support of the inner container 3 in the outer container 17, a support element, in particular a radial web, or a plurality of such support elements, in particular radial webs, to be arranged between the inner container 3 and the outer container 17, these supporting the inner container 3 on the inner surface 21 of the outer container 17. The outer container 17 is designed to be closed at its proximal end 33 at a distance from the proximal end 7 of the inner container 3, measured in the longitudinal direction of the container 1.

In the region of the connection point 27, which is arranged in the vicinity of the distal end 5 of the inner container 3 and is preferably offset from it in the proximal direction, the outer container 17 is connected to the inner container 3 in a gas-tight manner—in particular, fused to it. In this way, the peripheral volume 23 is enclosed in a gas-tight manner on all sides by the outer container 17.

It is also possible that the connection point 27—seen in the longitudinal direction of the container 1—is provided at the height of its distal end 5. In principle, it is also possible for the distal end 5 of the inner container 3 to be arranged inside the outer container 17, portions of the outlet channel section 25 then extending into the outer container 17, and for the connection point 27 to then be designed as a direct connection between the outer container 17 and the outlet channel section 25.

The longitudinal direction of the container 1 is in particular the direction in which the container 1 has its longest extension and/or the direction which points in the direction of an axis of symmetry of the container 1. In FIG. 1, this is the horizontal direction. A radial direction is perpendicular to the longitudinal direction. A circumferential direction concentrically surrounds the longitudinal direction.

The first porous separating element 9 closes off the inner container 3 at its proximal end 7. The second porous separating element 11 delimits the holding volume 15 in the region of the distal end 5 of the inner container 3.

The porous separating elements 9, 11 are spatially fixed on the inner container 3 and in particular spatially fixed to the inner shell surface 13 of the inner container 3, and consequently cannot be displaced in the inner container 3 or relative to the inner container 3. In particular, it is possible that the porous separating elements 9, 11 are integrally connected to the inner container 3, preferably fused.

The medical liquid arranged in the holding volume 15 can be dispensed from the distal outlet opening 31 via the valve device 29 in its open position, since the gas arranged under positive pressure in the peripheral volume 23 applies pressure to the medical liquid via the first porous separating element 9, wherein said pressure is greater than the ambient pressure in the external environment of the container 1. The medical liquid is therefore expelled through the distal outlet opening 31 in the open position of the valve device 29. This does not require any moving parts, in particular no displaceable stoppers, so that the container 1 is designed to be stopper-free, in particular having no displaceable stopper, very particularly no displaceable stopper made of a pharmaceutical rubber.

The expulsion of the medical liquid from the holding volume 15 can be interrupted by moving the valve device 29 from its open position to its closed position. In this way, multiple-use application of the medical liquid is possible, for example at different locations, for subcutaneous or intramuscular application, or over a longer period of time.

The peripheral volume 23 is preferably at least as large as the holding volume 15, preferably larger than the holding volume 15. As a result, the most homogeneous possible delivery of the medical liquid 15 via the distal outlet opening 31 can be guaranteed with a flow rate that is defined, optionally constant or varying in a certain way, over the entire delivery period.

The inner container 3 is preferably designed as a capillary, in particular with an inner diameter of less than 4 mm, preferably less than 3 mm. As a result, the liquid column of the medical liquid is advantageously held in the holding volume 15, which on the one hand makes it easier to fill the holding volume 15 and on the other hand prevents an air bubble forming when the medical liquid is being dispensed in the region of the distal end 5, and thus in particular in the region of the second porous separating element 11. Air or gas injection can thus advantageously be prevented. Even after the medical liquid has been completely dispensed from the holding volume 15, the second porous separating element 11, which is still wetted with the medical liquid, prevents gas from penetrating and being injected due to the capillary forces acting in it.

The capillary property of the inner container 3 also enables the holding volume 15 to be completely emptied, because the capillary forces hold the liquid column of the medical liquid together during emptying, so that it does not stick to the inner shell surface 13, but rather is completely released.

In the first exemplary embodiment of the container 1 shown in FIG. 1, the inner container 3 is elongated, in particular straight and preferably cylindrical, in particular in the form of a circular cylinder.

In the first exemplary embodiment of the container 1 according to FIG. 1, the outer container 17 is likewise cylindrical, preferably circular-cylindrical, except for the connection region in the region of the connection point 27.

The inner container 3 is filled in particular with the medical liquid, the outer container being filled with the gas under positive pressure. The gas can be air, but also an inert gas, in particular nitrogen, a noble gas, or a mixture of different gases, in particular nitrogen and/or at least one noble gas. If an oxygen-free or at least low-oxygen gas is arranged in the peripheral volume 23, the medical liquid can also be a liquid which is sensitive to oxygen. The container 1 is therefore also suitable for long-term storage of an oxygen-sensitive medical liquid, for example adrenaline. This is typically not the case in conventional medical containers with stoppers made of pharmaceutical rubber, since these stoppers have a certain permeability to oxygen—whereas the container 1 is gas-tight to the outside in the closed position of the valve device 29.

The first, proximal porous separating element 9 in this case is at least partially covered with a cover element 35 with respect to the peripheral volume 23 of the outer container 17, the cover element covering the proximal porous separating element 9 except for a central recess 37. The cover element 35 can in particular be designed as a cap with a central bore or as a membrane with a small opening. Alternatively, it is also possible for the first porous separating element 9 to be very small, that is to say with a small diameter, and to be arranged, in particular fused by melting, in a region of the inner shell surface 13 that is thickened radially inwards. The accordingly reduced area via which the first porous separating element 9 is in contact with the gas in the peripheral volume 23 advantageously reduces a transition of at least parts of the medical liquid into the vapor phase and thus a drying out of the proximal porous separating element 9.

A predetermined breaking point is preferably arranged in the area of the connection point 27. In this way, even if the container 1 is accidentally impacted, it is prevented from breaking explosively. Rather, a controlled escape of the gas from the peripheral volume 23 is preferably made possible—preferably without substantial leakage of the medical liquid. The predetermined breaking point is preferably designed as a bore or hole which is oriented transverse to the longitudinal direction, in particular in the radial direction. This prevents the container 1 from being accelerated essentially like a rocket by gas escaping from the peripheral volume 23. This results in at most one rotation of the container 1 about an axis that is perpendicular to the longitudinal axis, but no translational displacement. The predetermined breaking point increases the safety of the container 1 during operation.

The container 1 is preferably designed to hold small volumes of medical liquid, in particular less than 1 mL, preferably less than 0.6 mL, preferably less than 0.5 mL, preferably 1 mL. It is particularly preferably designed to hold a medical liquid which is intended for an ophthalmic injection, and in particular an injection into the vitreous body of an eye. In this case in particular, it is advantageous that the distal, second porous separating element 11 also has a filter effect due to its porous properties and can thus effectively prevent a particle injection into the eye.

The first porous separating element 9 and/or the second porous separating element 11, particularly preferably both porous separating elements 9, 11, is/are preferably designed as a sintered body, in particular as a frit, preferably as a glass frit or ceramic frit, or as a filter or filter membrane.

The distal, second porous separating element 11 is preferably arranged outside the outer container 17, in particular distally to the connection point 27. However, it is also possible for the distal, second porous separating element 11 to be arranged at the level of the connection point 27 or even in the outer container 17, as already described above.

The outlet channel section 25 is formed in this case in several parts with the inner container 3, whereby it is designed in particular as an attachment, preferably as a plastic attachment, which is placed tightly on the distal end 5 of the inner container 3 and is held there in particular by means of suitable holding and sealing means. Alternatively, however, it is also possible for the outlet channel section to be formed integrally with the inner container.

The outlet channel section 25 preferably has a suitable recess, in particular a transverse bore, for receiving the valve device 29.

FIG. 2 shows a schematic illustration of a second exemplary embodiment of the container 1. Identical and functionally-identical elements are provided with the same reference signs, so that reference is made to the previous description in this regard. In this second exemplary embodiment, the inner container 3, which is also preferably designed as a capillary, is drawn, in particular spirally drawn. This shortens the overall length of the container 1 with the same holding volume 15 and in particular with the same inner diameter of the inner container 3.

In the second exemplary embodiment, the outer container 17 is in particular barrel-shaped or piston-shaped, convex and preferably ovoid or oval. In particular, it has a curved wall which has a finite, non-zero curvature in at least two mutually perpendicular directions. With this geometry, the outer container 17 is particularly pressure-stable, in particular since it has no corners or sharp transitions.

FIG. 3 shows a schematic detailed illustration of a third exemplary embodiment of the container 1. Identical and functionally-identical elements are provided with the same reference signs, so that reference is made to the previous description in this regard. A preferred mode of operation and configuration of the valve device 29 is explained in more detail with reference to FIG. 3. The valve device 29 here has a combination valve 39 with a check valve 41 and a manually operated valve 43, which are formed integrally with one another as a valve device 29. The check valve 41 has a check valve element 45, which in this case is designed in particular as a valve ball, which is in particular spherical. This check valve element 45 is forced by a positive pressure in the holding volume 15 into a valve seat 47, which is formed at least partially in a valve element 49 of the manually operated valve 43. This valve element 49 is preferably designed as a cylinder rotatably mounted in the outlet channel section 25 about a valve axis of rotation, the valve axis of rotation pointing in the radial direction and thus being perpendicular to the longitudinal direction of the container 1. The valve seat 47 is formed in the valve element 49 as a recess or trough, thus as a depression in an outer peripheral surface 51 of the valve element 49.

The valve element 49 is—in this case as one piece—connected to an actuating element 53, in particular a handle, wherein the valve element 49 can be pivoted about the valve axis of rotation by the actuating element 53, in particular by hand.

FIG. 3 shows the combination valve 39 and thus the valve device 29 in its/their closed position. Because the check valve element 45 is pressed into the valve seat 47 by the positive pressure in the holding volume 15, the holding volume 15 is sealed off from the distal outlet opening 31.

If the valve element 49 is pivoted about the valve axis of rotation—in particular by 90°—the outer circumferential surface 51 outside the recess forming the valve seat 47 pushes the check valve element 45 in the direction of the holding volume 15, thus to the right in FIG. 3, so that it is displaced out of the valve seat 47. As a result, the blocking action of the check valve element 45 is overcome. At the same time, the recess of the valve element 49 forming the valve seat 47 now provides a fluid path via which the holding volume 15 is in fluid communication with the distal outlet opening 31. The combination valve 39 and thus also the valve device 29 is accordingly arranged in the open position. A shift back to the closed position is carried out in a simple manner such that the valve element 49 with the valve seat 47 is brought back into a position in which the check valve element 45 can be received in the valve seat 47 and create a seal—in particular into the position shown in FIG. 3.

The valve element 49 is mounted in a fluid-tight manner in the outlet channel section 25, in particular via a seal 55, which in this case is designed in particular as an O-ring.

As an alternative to the configuration shown here, the valve device 29 can also have a check valve, a manually operated valve, or a check valve and a manually operated valve, which are formed separately from one another, or a switching valve.

Figure 4:
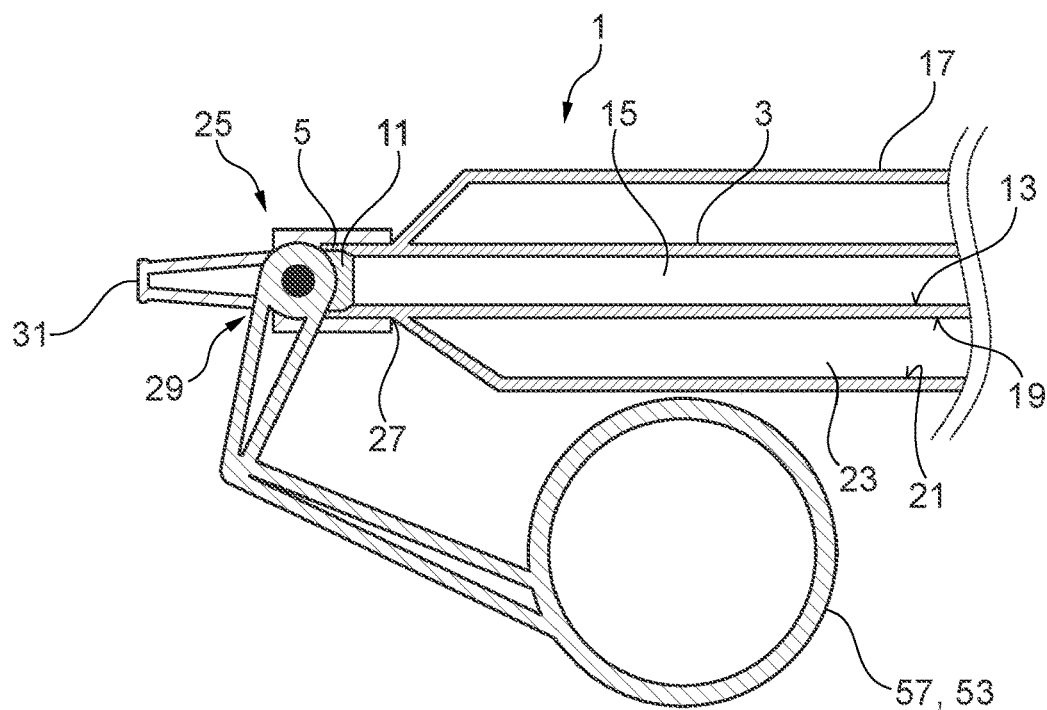
FIG. 4 shows a detailed schematic representation of a fourth embodiment of a container for medical liquids.

FIG. 4 shows a schematic illustration of a fourth exemplary embodiment of the container 1. Identical and functionally-identical elements are provided with the same reference signs, so that reference is made to the previous description in this regard. In this fourth exemplary embodiment, the container 1 has a finger trigger 57 as an actuating element 53 for the valve device 29. As a result, the valve device 29 can be actuated in a particularly ergonomic manner, in particular when a patient administers an injection to himself from the container 1.

An exemplary embodiment of the container 1, which is not shown, is also preferred in which the outlet channel section 25 is arranged at a finite angle other than 0° to the primary direction of extension, and in particular to the longitudinal direction, of the inner container 3. In this way, a quasi-pistol-like configuration of the container 1 can be provided, which can be operated particularly ergonomically and in particular with a comfortable hand position. This pistol-like configuration of the container 1 is preferably combined with a finger trigger 57 as an actuating element 53 for the valve device 29, which further increases the ergonomics of the container 1 and increases its usability, in particular also for patients with restricted mobility who want to perform an injection themselves.

A method for filling the container 1 preferably provides that the peripheral volume 23 is filled with a gas at a first predetermined pressure which is greater than an expected external ambient pressure when the container 1 is used later, in particular therefore above a normal pressure of, in particular, 1013 mbar, wherein the holding volume 15 of the inner container 3 is then filled with a medical liquid at a second predetermined pressure, the second predetermined pressure being greater than the first predetermined pressure. In particular, the combination of the pressure conditions mentioned here and the capillary properties of the holding volume 15 results in a complete filling of the same up to the first, proximal, porous separating element 9, without air bubbles. The valve device 29 is then preferably closed and the filling is ended. As a result, the second predetermined pressure prevails as the final pressure, and consequently as a positive pressure in the peripheral volume 23 and in the holding volume 15. The injection properties of the container 1 and in particular at least an initial flow rate for a discharge of the medical liquid from the distal outlet opening 31 can thus be set by selecting the second predetermined pressure. The first predetermined pressure preferably defines a final pressure at the end of the injection.

Before the peripheral volume 23 is filled or when the peripheral volume 23 is filled, a partial pressure in the gas of at least one main component of the medical liquid, in particular a solvent, is preferably set such that this partial pressure corresponds to the vapor pressure of the medical liquid or at least the main component of the medical liquid in the inner container 3 at the second predetermined pressure. Consequently, a saturation vapor pressure is set in the peripheral volume 23 under storage conditions for the medical liquid, so that evaporation of the same into the peripheral volume 23 via the first porous separating element 9, and thus a drying out of the first porous separating element 9, is avoided.

The container 1 proposed here provides an injection container which is particularly suitable for self-use by patients. In this case, the operator of the container 1 does not have to apply a pressure in order to expel the medical liquid from the holding volume 15. Last but not least, this also enables the presetting of a suitable flow rate for the expulsion of the medical liquid on the part of the filler of the container 1.

The container 1 is preferably set up for use in an auto-injection device, in particular an auto-injector or pen, or is itself designed as an auto-injection device.

Because the valve device 29 is arranged on the outlet channel section 25 and thus distally on the container 1, it is arranged close to a cannula provided for injection and connected to the distal outlet opening 31. It is also possible for an operator of the container 1 to grip it close to the valve device 29 and the outlet channel section 25, so that ergonomic one-hand operation is possible.

The container 1 is characterized in particular by very low dead air volumes. It is therefore not necessary to eject air before an injection.

Since there are no displaceable stoppers, no lubricant is required, such that there is no need to use silicone oil.

The valve device 29 is preferably biased into its closed position, so that active actuation is only required in the direction of the open position. This additionally simplifies the operation of the container 1.

In particular, due to the capillary design of the inner container 3 and its accordingly elongated geometry, an accurate reading of even small dosages is readily possible. This, in combination with the bubble-free filling and the elimination of the need to eject air from the container 1 before an injection, enables extremely economical use of the medical liquid arranged in the holding volume 15. The medical container 1 can therefore be used advantageously not only for small injection volumes, but also for use in connection with expensive or toxic substances. The container 1 enables in particular an ergonomically favorable and simple injection.

It is particularly suitable for precise, complex injections, especially in ophthalmology and/or surgery.

The invention claimed is:

1. A container for medical liquids, the container comprising:
    an inner container having a distal end and a proximal end;
    a first porous separating element arranged at the proximal end of the inner container; and
    the first porous separating element delimiting a holding volume for holding a medical liquid; and
    an outer container in which the inner container is arranged with the proximal end and with at least portions of the holding volume,
    the outer container extending around the inner container in a gas-tight manner, such that a gas under positive pressure is arranged in a peripheral volume between an outer surface of the inner container and an inner surface of the outer container,
    wherein an outlet channel section is connected to the distal end of the inner container and the outlet channel section includes a connection element for an injection device,
    wherein a valve device is arranged in the outlet channel section, the valve device operative in an open position to open a fluid connection between a distal outlet opening of the outlet channel section and the holding volume and in a closed position to block the fluid connection between the distal outlet opening and the holding volume, and
    wherein the container is adapted for injecting medical liquids.

2. The container according to claim 1, wherein a second porous separating element is arranged at the distal end, the first porous separating element and the second porous separating element delimiting the holding volume.

3. The container according to claim 1, wherein the inner container has a design selected from a group consisting of:
   a) a capillary,
   b) elongated,
   c) straight,
   d) spiral, and
   e) combinations thereof.

4. The container according to claim 1, wherein the outlet channel section is formed integrally with the inner containers or in several pieces.

5. The container according to claim 2, wherein at least one of the first porous separating element and the second porous separating element is a sintered body.

6. The container according to claim 2, wherein the second porous separating element is arranged outside the outer container.

7. The container according to claim 1, wherein the outer container has a shape selected from a group consisting of:
   a) cylindrical,
   b) barrel-shaped or piston-shaped,
   c) at least partially convex or, completely convex,
   d) ovoid or oval, and
   e) combinations thereof.

8. The container according to claim 1, wherein the outlet channel section is arranged at a finite angle other than 0° to a primary direction of extension of the inner container.

9. The container according to claim 1, wherein the container has a finger trigger which is operatively connected to the valve device in such a way that the valve device is actuated by the finger trigger.

10. The container according to claim 1, wherein the valve device is selected from a group consisting of:
    a) a check valve,
    b) a manually operated valve,
    c) a switching valve, and
    d) a combination valve comprising a check valve and a manually operated valve.

11. The container according to claim 1, wherein the inner container is filled with a medical liquid, the outer container being filled with a gas under positive pressure.

12. The container according to claim 1, wherein the first, proximal porous separating element is covered with respect to the peripheral volume of the outer container by a cover element at least in regions, wherein the cover element covers the first porous separating element.

13. The container according to claim 1, wherein a predetermined breaking point is arranged at a distal connection point between the outer container and the inner container.

14. The container according to claim 1, wherein the container is designed as a syringe or carpule.

15. The container of claim 1, wherein at least one of the first porous separating element and the second porous separating element is selected from a group consisting of a glass frit a ceramic frit, a filter and a filter membrane.

16. The container of claim 1, wherein at least portions of the outlet channel section are arranged outside the outer container.

17. The container of claim 3, wherein the design of the inner container is the capillary.

18. The container of claim 1, further comprising a cover element covering the first porous separating element in an axial direction, the cover element including a central opening.

19. The container of claim 1, wherein the container includes a holding volume of less than 2.0 ml.

20. A method for filling a container for injecting medical liquids according to claim 1, the method comprising:
    filling the peripheral volume of the container with a gas at a first predetermined pressure,
    filling the holding volume of the inner container with a medical liquid at a second predetermined pressure which is greater than the first predetermined pressure, and
    closing the valve device.

* * * * *